(12) United States Patent
Wang et al.

(10) Patent No.: US 7,702,075 B2
(45) Date of Patent: Apr. 20, 2010

(54) ENERGY SPECTRUM MODULATION APPARATUS, MATERIAL DISCRIMINATION METHOD AND DEVICE, IMAGE PROCESSING METHOD

(75) Inventors: Xuewu Wang, Beijing (CN); Yinong Liu, Beijing (CN); Zhiqiang Chen, Beijing (CN); Yaohong Liu, Beijing (CN); Huaqiang Zhong, Beijing (CN); Dongsheng Zhang, Beijing (CN); Yumei Chen, Beijing (CN); Feng Gao, Beijing (CN)

(73) Assignees: Tsinghu University, Beijing (CN); Nuctech Company Limited, Beijing (CN)

( * ) Notice: Subject to any disclaimer, the term of this patent is extended or adjusted under 35 U.S.C. 154(b) by 32 days.

(21) Appl. No.: 11/788,995

(22) Filed: Apr. 23, 2007

(65) Prior Publication Data

US 2007/0286329 A1 Dec. 13, 2007

(30) Foreign Application Priority Data

May 19, 2006 (CN) .................. 2006 1 0011945

(51) Int. Cl.
*H05G 1/64* (2006.01)
*G01N 23/087* (2006.01)
*G21K 3/00* (2006.01)

(52) U.S. Cl. .................. 378/98.9; 378/53; 378/56; 378/57; 378/158

(58) Field of Classification Search .............. 378/5, 378/98.9, 98.11, 98.12, 156, 157, 158, 159, 378/51, 53, 54, 56, 57
See application file for complete search history.

(56) References Cited

U.S. PATENT DOCUMENTS

| | | | | |
|---|---|---|---|---|
| 4,277,685 | A * | 7/1981 | Covic et al. ............... | 378/7 |
| 4,686,695 | A * | 8/1987 | Macovski ................ | 378/146 |
| 5,040,199 | A * | 8/1991 | Stein ...................... | 378/56 |
| 5,044,002 | A   | 8/1991 | Stein ...................... | 378/54 |
| 5,204,888 | A * | 4/1993 | Tamegai et al. .......... | 378/53 |
| 5,319,547 | A * | 6/1994 | Krug et al. ............... | 705/13 |
| 5,524,133 | A   | 6/1996 | Neale ..................... | 378/53 |
| 5,661,774 | A * | 8/1997 | Gordon et al. ........... | 378/101 |
| 5,768,334 | A * | 6/1998 | Maitrejean et al. ...... | 378/53 |
| 6,069,936 | A   | 5/2000 | Bjorkholm ............. | 378/98.9 |
| 6,173,038 | B1* | 1/2001 | Siffert et al. ............ | 378/56 |
| 6,226,352 | B1* | 5/2001 | Salb ...................... | 378/98.9 |

(Continued)

FOREIGN PATENT DOCUMENTS

WO WO 00/43760 7/2000

*Primary Examiner*—Allen C. Ho
(74) *Attorney, Agent, or Firm*—Westman, Champlin & Kelly, P.A.

(57) ABSTRACT

Disclosed are an energy spectrum modulation apparatus, a material discrimination method and a device thereof, as well as an image processing method are disclosed, which can discriminate the material in large- and medium-sized objects such as cargo containers, air cargo containers, etc. by using X-rays having different energy levels. The energy spectrum modulation apparatus comprises a first energy spectrum modulation part for modulating a first ray having a first energy spectrum, and a second energy spectrum modulation part coupled to the first energy spectrum modulation part and for modulating a second ray having a second energy spectrum different from the first energy spectrum. The present invention can be used in the non-opening inspection for large-sized container cargo at places such as Customs, ports and airports.

17 Claims, 4 Drawing Sheets

U.S. PATENT DOCUMENTS

| | | | |
|---|---|---|---|
| 6,246,747 B1 * | 6/2001 | Wear et al. | 378/98.9 |
| 6,252,932 B1 * | 6/2001 | Arakawa | 378/98.9 |
| 6,487,274 B2 * | 11/2002 | Bertsche | 378/143 |
| 6,597,758 B1 * | 7/2003 | Rosner | 378/53 |
| 6,614,878 B2 * | 9/2003 | Bogatu et al. | 378/158 |
| 6,950,492 B2 * | 9/2005 | Besson | 378/5 |
| 6,968,030 B2 * | 11/2005 | Hoffman | 378/5 |
| 7,050,529 B2 * | 5/2006 | Hoffman | 378/5 |
| 7,120,222 B2 * | 10/2006 | Hoffman | 378/5 |
| 7,187,756 B2 * | 3/2007 | Gohno et al. | 378/124 |
| 7,257,188 B2 * | 8/2007 | Bjorkholm | 378/53 |
| 7,330,535 B2 * | 2/2008 | Arenson et al. | 378/158 |
| 7,463,715 B2 * | 12/2008 | Spahn | 378/98.12 |
| 2003/0195416 A1 * | 10/2003 | Toth | 600/427 |

* cited by examiner (A)

(B)

ENERGY SPECTRUM MODULATION APPARATUS, MATERIAL DISCRIMINATION METHOD AND DEVICE, IMAGE PROCESSING METHOD

FIELD OF THE INVENTION

The present invention relates to radiograph imaging inspection for large-sized objects, more particularly to a energy spectrum modulation apparatus, a material discrimination method and a device thereof, as well as an image processing method, which can discriminate the material in large- and medium-sized objects such as cargo containers, air cargo containers, etc. by using radiations having different energy levels.

BACKGROUND OF THE INVENTION

The present application claims priority of Chinese patent application Serial No. 200610011945.9, filed May 19, 2006, the content of which is hereby incorporated by reference in its entirety.

The existing cargo inspection system based on radiographic imaging generally causes a single energy ray to interact with the object under inspection, and then detects the ray having penetrated through the object under inspection to obtain an image. Although such a system can reflect the change in shape and mass thickness (i.e., mass per unit area obtained by multiplying a thickness t by a density) of the object under inspection, it can't discriminate the material of the object under inspection.

The dual-energy detection method for distinguishing the material attributes of objects has been proposed for a long time as disclosed in U.S. Pat. No. 5,044,002, and within low energy region, the method has been widely applied to various fields such as osteoporosis diagnosis, geographic oil layer detection and material discrimination for small objects. However, it has long been recognized that within high energy region (>1 MeV) the slight difference caused by electron pair effect is insufficient to implement material discrimination, thereby having a poor practicability.

In 1990s, U.S. Pat. No. 5,524,133 disclosed that the angular distribution of Compton scatter effect and the isotropy of electron pair effect were used to analyze the scatter components of X-rays caused by each effect after the X-rays interacted with an object, thereby discriminating the substance's atomic number of the object interacting with the X-rays. In U.S. Pat. No. 5,524,133, high-energy X-rays is caused to interact with a target having a greater atomic number after interacting with the object. Then several detectors are positioned at different angles with respect to the target so as to detect Compton scatter effect and electron pair effect. Nevertheless, since it is very difficult to detect the scatter after interaction between the target and the X-rays, which have penetrated through the object, a large incident dose of X-rays is usually required. In addition, the SNR (signal to noise ratio) of detection signals is rather low because the detector array arranged at such angles within the same horizontal plane is susceptible to the interference from its neighbor channel. The above disadvantages have an adverse impact on the determination of the substance's atomic number, and the image quality is unsatisfactory. Thus this method has not been put into practical application since proposed in 1993.

Later in U.S. Pat. No. 6,069,936 and international application WO 00/43760 a high-energy radiation source is employed to generate X-rays, which are filtered by means of specific materials to obtain another ray having a higher energy spectrum. The penetrating X-rays having two energy spectra are detected after they interact with the substance. The substance's atomic number and material type are then determined by computing the ratio between the two detection values.

During the X-rays having two energy spectra interact with the inspected object in this method, as the inspected object grows in thickness, the two energy spectra of the X-rays, which have penetrated through the inspected object, have an ever-decreasing difference and rapidly become identical to each other. In this case, it can't discriminate the inspected object any more.

SUMMARY OF THE INVENTION

In view of the problems in the prior art, the present invention is accomplished. It is an object of the present invention to generate in high energy range (>1 MeV) two beams of X-rays of which energy spectra have principal energy levels distinct from each other, detect the penetration radiation of the two X-ray beams after their interaction with an object at the same position and determine the effective atomic number range of the material of the object based on the two detection values, thereby implementing the non-destructive inspection for the object.

At an aspect of the present invention, there is provided an energy spectrum modulation apparatus comprising: a first energy spectrum modulation part for modulating a first ray having a first energy spectrum; and a second energy spectrum modulation part coupled to the first energy spectrum modulation part for modulating a second ray having a second energy spectrum different from the first energy spectrum.

According to an embodiment of the present invention, at least one of the first energy spectrum modulation part and the second energy spectrum modulation part is coupled onto a rotation shaft.

According to an embodiment of the present invention, the first energy spectrum modulation part includes at least one first vane, and the second energy spectrum modulation part includes at least one second vane.

According to an embodiment of the present invention, the first vane is made of high Z material.

According to an embodiment of the present invention, the first vane is made of at least one of Pb, W, U and Cu.

According to an embodiment of the present invention, the second vane is made of low Z material.

According to an embodiment of the present invention, the second vane is made of at least one of B, C, polyethylene and any other hydrogen-rich organic material.

According to an embodiment of the present invention, the first vane and the second vane are arranged alternately and can rotate.

According to an embodiment of the present invention, the mass thickness of the first vane is smaller than or equal to that of the second vane in the direction of the rays.

At another aspect of the present invention, there is provided a method of discriminating material using rays having different energy levels comprising the steps of: generating alternately a first ray having a first energy spectrum and a second ray having a second energy spectrum; performing energy spectrum modulation for the first ray and second ray respectively by the energy spectrum modulation apparatus described above; utilizing the modulated first ray and second ray to interact with an inspected object; collecting the first ray and the second ray after their interaction with the inspected object to obtain a first detection value and a second detection value; and discriminating the material of the inspected object based on the first detection value and the second detection value.

According to an embodiment of the present invention, the discriminating step includes generating corresponding classification functions from the first detection value and the second detection value, and determining the material of the inspected object based on the classification functions.

According to an embodiment of the present invention, the classification functions is fitting functions of the detection values obtained after the first ray and the second ray interact respectively with predetermined known materials in the case of their mass thickness varying.

According to an embodiment of the present invention, the detection values are the transmission intensity of the rays after they penetrate through the inspected object.

According to an embodiment of the present invention, the known materials are different materials which represent organic matter, light metal, inorganic matter and heavy metal respectively and whose atomic numbers are known.

According to an embodiment of the present invention, the method further comprises collecting the first ray and the second ray after their interaction with the inspected object by a variable gain detector.

According to an embodiment of the present invention, the gain of the detector at the time of detecting the first ray is different from that at the time of detecting the second ray.

At another aspect of the present invention, there is provided an device for discriminating material using rays having different energy levels comprising: a ray generation apparatus for generating alternately a first ray having a first energy spectrum and a second ray having a second energy spectrum; the energy spectrum modulation apparatus for modulating the first ray and the second ray respectively, wherein the modulated first ray and the modulated second ray interact with the inspected object; a collecting apparatus for collecting the first ray and the second ray after their interaction with the inspected object to obtain a first detection value and a second detection value; and a material discrimination apparatus for discriminating the material of the inspected object based on the first detection value and the second detection value.

According to an embodiment of the present invention, the discriminating includes generating corresponding classification functions from the first detection value and the second detection value, and determining the material of the inspected object based on the classification functions.

According to an embodiment of the present invention, the classification functions are fitting functions of the detection values obtained after the first and second rays interact respectively with predetermined known materials in the case of their mass thickness varying.

According to an embodiment of the present invention, the detection values are the transmission intensity of the rays after they penetrate through the inspected object.

According to an embodiment of the present invention, the known materials are different materials which represent organic matter, light metal, inorganic matter and heavy metal respectively and whose atomic numbers are known.

According to an embodiment of the present invention, the collecting apparatus has a variable gain.

According to an embodiment of the present invention, the gain of the collecting apparatus at the time of detecting the first ray is different from that at the time of detecting the second ray.

At another aspect of the present invention, there is provided an image processing method comprising steps of utilizing a first ray having a first energy spectrum and a second ray having a second energy spectrum to interact with an inspected object, respectively, wherein the first ray and the second ray are modulated by the energy spectrum modulation apparatus described above; collecting the first ray and the second ray after the interaction to obtain a first detection value and a second detection value; comparing the first detection value and the second detection value with a threshold value respectively to judge the mass thickness information of the inspected object; and based on the mass thickness information, combining an image obtained from the first detection value and an image obtained from the second detection value with different weighting factors.

According to an embodiment of the present invention, the mass thickness information is determined based on the attenuation of the rays from the inspected object.

According to an embodiment of the present invention, for the material of small mass thickness, the weighting factor for the image from the first detection value is smaller than that for the image from the second detection value.

According to an embodiment of the present invention, for the material of large mass thickness, the weighting factor for the image from the first detection value is greater than that for the image from the second detection value.

The two different energy spectra of the rays, which are generated alternately by the device of the present invention, are predominated by X-rays with distinct energy difference. This benefits the discrimination for a thick inspected object. In addition, optimized energy spectra of high- and low-energy rays are obtained by subjecting the generated high- and low-energy X-rays to energy spectrum modulation with different absorbing materials, which further widens the equivalent energy difference between the two X-ray beams and thus improves the discrimination accuracy for materials, particularly for the materials of small mass thickness.

Further, for the different single pulse doses and energy levels of the high- and low-energy rays, the variable gain detector adjusts the amplifying gain to widen the dynamic range. This can further improve the detection effect of the same detector for rays having different energy levels, and thereby increase the detection accuracy.

DETAILED DESCRIPTION OF THE PREFERRED EMBODIMENTS

Hereafter, an embodiment of the present invention is described in detail with reference to the drawings.

Figure 1:
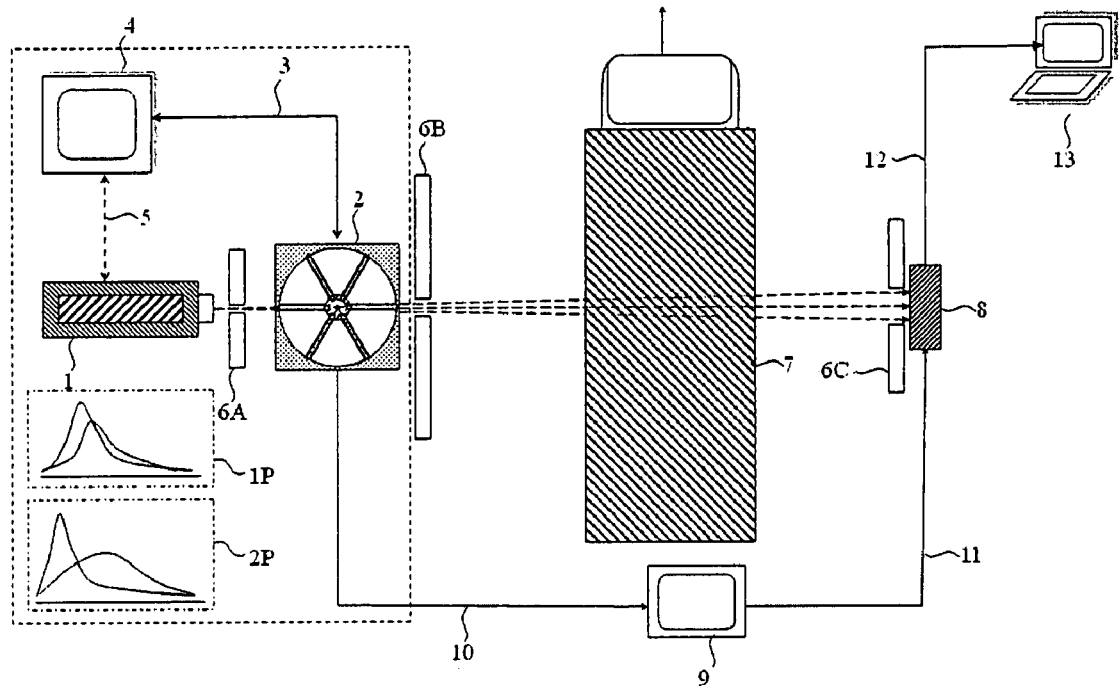
FIG. 1 is the schematic structural view of a material discrimination system according to the present invention.

FIG. 1 is the schematic structural view of a material discrimination system according to an embodiment of the present invention.

As shown in FIG. 1, the material discrimination system according to the present invention comprises a RF linac (linear accelerator) 1, an energy spectrum modulation apparatus 2, a synchronization control part 4 connected to the RF linac 1 and the energy spectrum modulation apparatus 2 via line 3, a first collimator 6A, a second collimator 6B, a third collimator 6C, a control part 9 connected to the energy spectrum modulation apparatus 2 via line 10, a detector 8 connected to the control part 9 via line 11, and a material discrimination and image processing part 13 connected to the detector 8 via line 12.

In the present embodiment, the RF linac 1 alternately generates X-rays having two different energy levels. The X-rays each interact with and penetrate through the same inspected object 7, and then detected by the detector 8. The detection results of the detector 8 are analyzed by the computer 13 to obtain the radiation images of the inspected object and to further distinguish the material attributes of the inspected object.

As shown in FIG. 1, the synchronization control part 4 establishes a session 5 with the RF linac 1. After status confirmation, the RF linac 1 alternately generates two kinds of X-rays having different energy levels based on the cycle parameters and control signals provided by the synchronization control part 4. The energy spectrum 1 P of the X-rays generated by the RF linac 1 has a distinct energy difference. However, such a difference can't satisfy the requirement of the system application, the energy spectrum modulation is needed for the energy spectrum 1 P to obtain the energy spectrum of high- and low-energy rays having a wider energy difference.

Therefore, based on the trigger signals, the RF linac 1 can alternately generate X-rays of two different energy spectra in which different energy levels predominate respectively. Since the spectrum of the X-rays generated by the accelerator is wide, energy spectrum modulation is needed to further increase the proportion of X-rays with desired energy levels in the spectrum. Considering the energy levels of the X-rays generated by the RF linac 1, various materials can be utilized to perform energy spectrum modulation, thereby obtaining the energy spectra most suitable for material discrimination.

In addition, since the energy distribution domains vary in the energy spectra of the X-rays, the materials suitable for energy spectrum modulation differ. For example, when the lower limit of the principal domain of an X-ray beam's energy distribution is higher than a threshold value (e.g., ~3 MeV) of higher energy level, a low Z material, such as B, C, polyethylene and any other hydrogen-rich organic material, should be chosen for energy spectrum modulation of this X-ray beam.

Meanwhile, in order to absorb the scatter component of low energy level in the rays, it is preferred to additionally utilize a thin high Z material for energy spectrum modulation after using a thick low Z material for energy spectrum modulation. When the lower limit of the principal domain of an X-ray beam's energy distribution is higher than a threshold value (e.g., ~300 keV) of lower energy level, a high Z material, such as Pb, W, U, etc., should be chosen for energy spectrum modulation of this X-ray beam; a medium Z material such as Cu can also be chosen.

Figure 2:
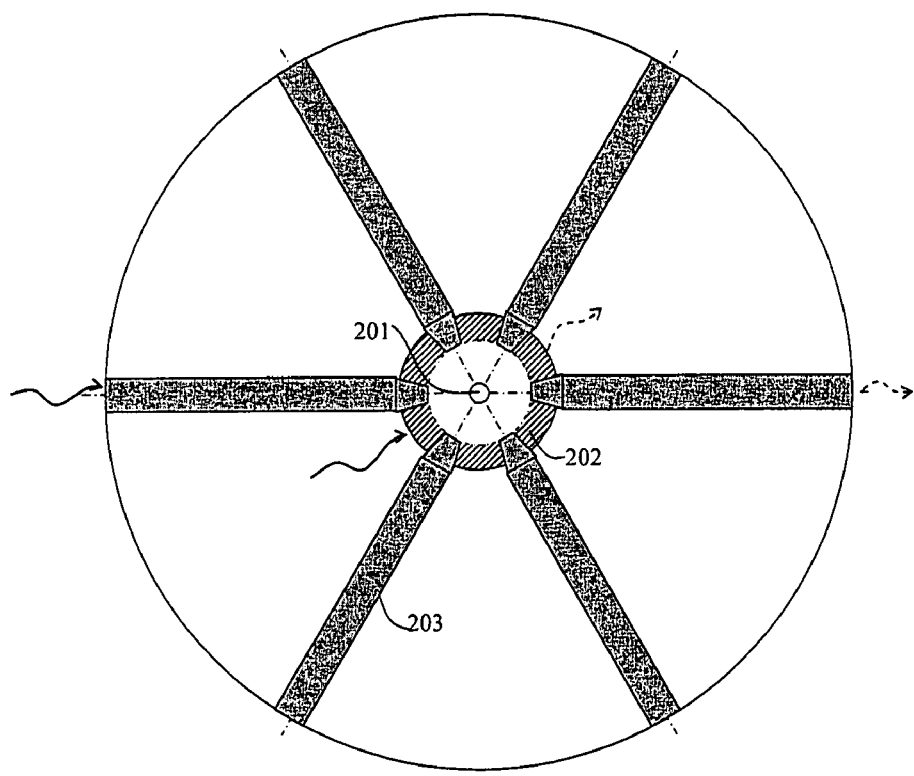
FIG. 2 is the sectional view of the energy spectrum modulation apparatus in the material discrimination system shown in FIG. 1.

FIG. 2 is the plan view of the energy spectrum modulation apparatus 2 in the material discrimination apparatus shown in FIG. 1. As shown in FIG. 2, the energy spectrum modulation apparatus 2 comprises a rotation shaft 201 coupled to a servo motor, a first energy spectrum modulation part 202 disposed on the rotation shaft 201, a second energy spectrum modulation part 203 coupled to the first energy spectrum modulation part 202, and a position detector (not shown).

Here, the first energy spectrum modulation part 202, which is made of high Z material and coupled to the rotation shaft 201, is used for energy spectrum modulation of the low-energy rays. As shown in FIG. 2, the first energy spectrum modulation part 202 includes a number of sections spaced from each other with each section being referred as a short vane. In this case, the first energy spectrum modulation part 202 can be coupled onto the second energy spectrum modulation part 203, while the second energy spectrum modulation part 203 can be coupled directly onto the rotation shaft 201. Otherwise, as an alternative aspect, the vanes of the first energy spectrum modulation part 202 can be made as required in a similar shape to that of the vanes of the second energy spectrum modulation part 203. In this way, the first and the second energy spectrum modulation parts 202 and 203 can both be coupled onto the rotation shaft 201.

The second energy spectrum modulation part 203, which is made of low Z material such as compound material, for example a material made of polyethylene plus Pb, which has a low average Z value, and formed into one or several vanes, is used for energy spectrum modulation of the high-energy ray. As shown in FIG. 2, the mass thickness of the vanes of the second energy spectrum modulation part 203 is greater than that of the first energy spectrum modulation part 202 in the direction of ray emission.

To implement energy spectrum modulation, the vanes rotate around the axis at a preset frequency, and the position detector generates a trigger signal as a synchronization signal when detecting that the vanes rotate to a fixed position. The signal is sent to the synchronization control part 4 and the control part 9 via line 3 and 10 respectively, and the RF linac 1 and the detector 8 are made synchronized with the energy spectrum modulation apparatus 2 under the control of the synchronization control part 4 and the control part 9 respectively.

In this way, it can be ensured that the rays having a high-energy spectrum all interact with the material of the vanes, i.e., they all undergo the modulation by the second energy spectrum modulation part 203, while all the rays of a low-energy spectrum are subjected to the absorption by the material on the axis, i.e., they all undergo the modulation by the first energy spectrum modulation part 202.

As above described, the material of the first energy spectrum modulation part 202 can be a high Z material such as Pb, W, U, etc., which is selected as the material for energy spectrum modulation of X-rays; a medium Z material such as Cu can also be selected. On the contrary, the material of the second energy spectrum modulation part 203 can be a low Z material such as B, C, polyethylene and any other hydrogen-rich organic material, which is selected as the material for energy spectrum modulation of X-rays. As a result of the modulation, the energy spectra 2 P of high- and low-energy rays are obtained, where the energy spectra of two different energy levels are taken sufficiently apart from each other.

Figure 3:
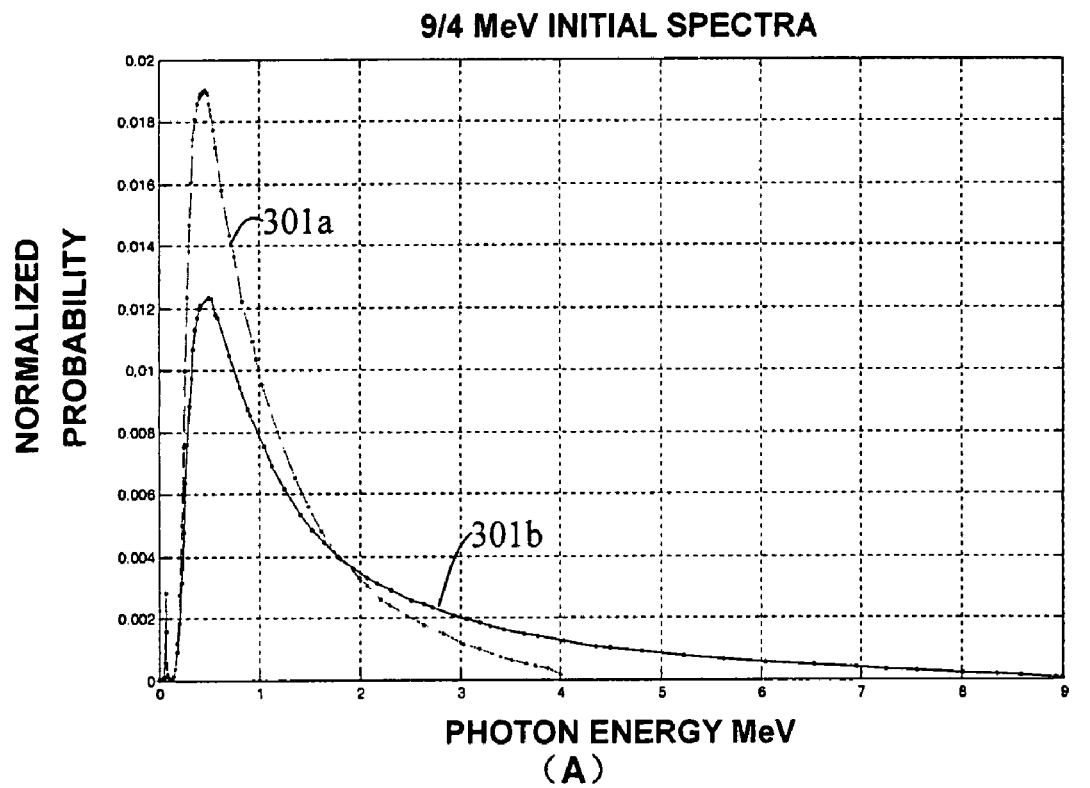
FIG. 3 is the schematic views of the energy spectra generated by an accelerator and the dual-energy spectra after being modulated.
Figure 3:
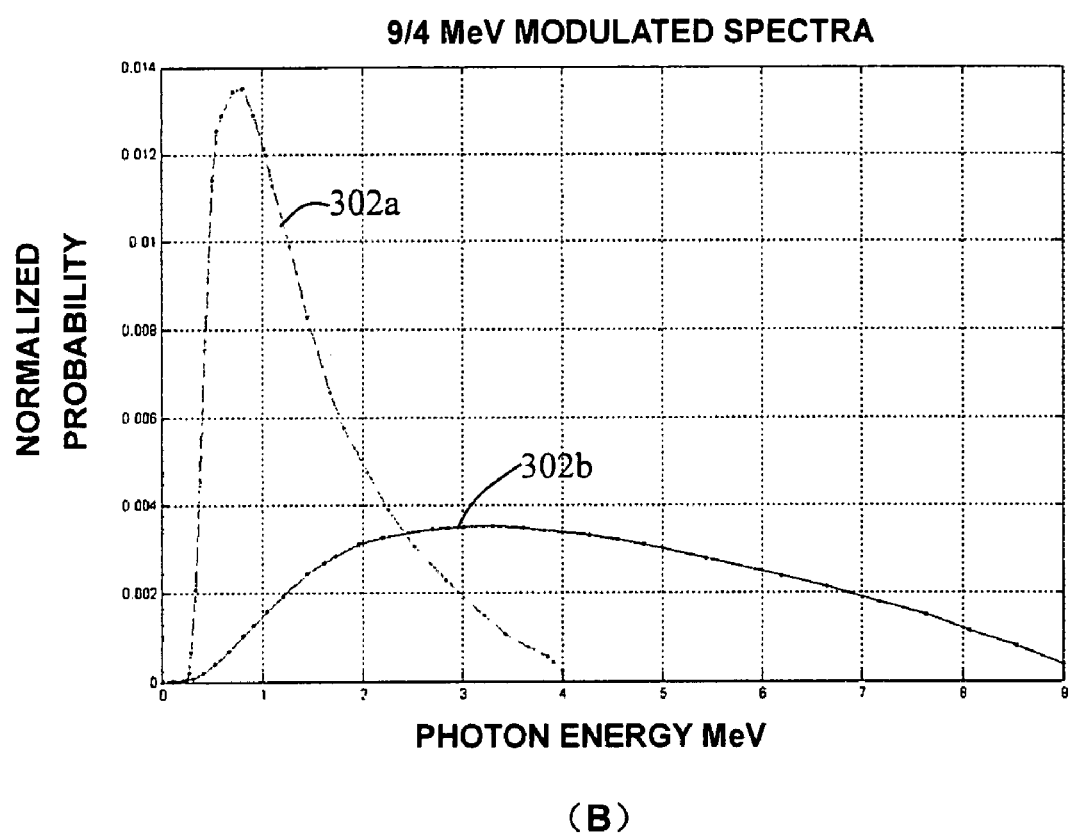

Further, FIG. 3 is the schematic views of the energy spectra generated by the accelerator and the dual-energy spectra obtained after the modulation, respectively. As shown in FIG. 3(A), the energy spectra before the modulation are illustrated as normalized Curves 301a and 301b which represent the energy spectra generated by the dual-energy accelerator with the high energy level being 9 MeV and the low energy level being 4 MeV; as shown in FIG. 3(B), the energy spectra after the modulation are illustrated as normalized Curves 302a and 302b. It can be seen in this diagram that the difference between the two energy spectra is further widened.

The optimized rays having both high and low energy levels, which are obtained after the modulation by the energy spectrum modulation apparatus 2, pass through the first and second collimators 6A and 6B and then interact with the inspected object 7. As shown in FIG. 1, the inspected object 7 moves along a fixed path and a fixed direction perpendicular to the radiation plane. Having penetrated through the inspected object 7, the rays pass through the third collimator 6C and then are collected by the detector 8, which collects data of high and low energy levels, such as the transmission intensity of the rays after radiating the object, based on the synchronization signal of the control system 9. In addition, based on an external trigger signal, the detector 8 can change the multiple of its amplifying gain to change its dynamic range, thereby obtaining with higher accuracy the signal values after the interaction between the dual-energy rays and the object, and accurately recognizing the difference of the dual-energy rays after their interaction with the object. For example, in the case of the rays having different energy levels, the detector 8 has different multiples of amplifying gain.

The data signals outputted from the detector 8 is sent to the material discrimination and image processing part 13 via line 12. As described above, the detection values by the detector 8 are a detection value HEL for high energy level and a detection value LEL for low energy level. The obtained detection values HEL and LEL can be substituted into classification functions to determine the effective atomic number range of the material in the inspected object, thereby determining the material attributes.

Figure 4:
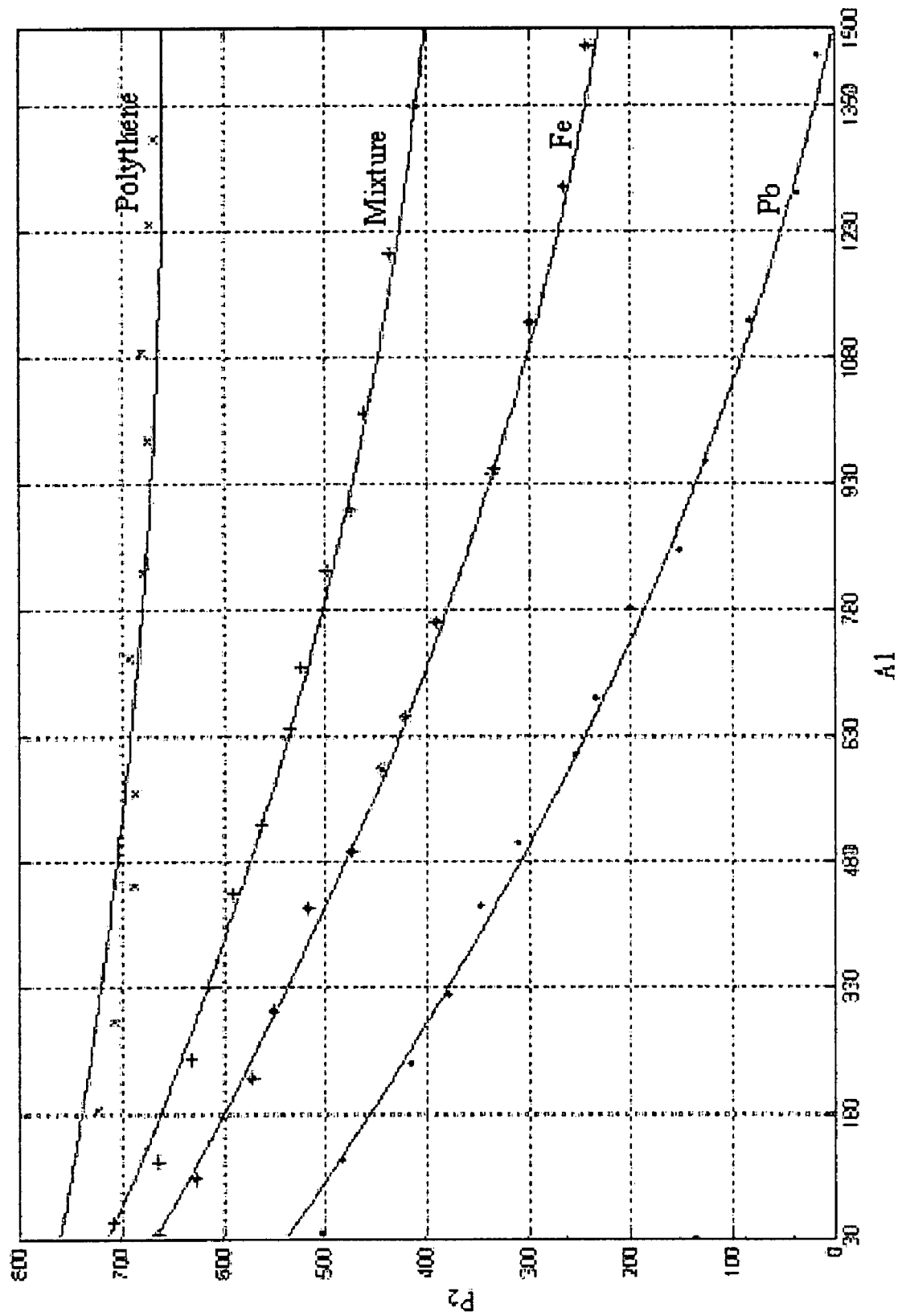
FIG. 4 shows the function relationship curves between radiation energy and the attributes and mass thickness of materials within the overall energy range.

Here, the classification functions are acquired as follows: using the rays with two energy levels from the dual-energy system to scan an atomic-number-known material, such as polyethylene standing for organic matter, Al for light metal, Fe for inorganic matter and Pb for heavy metal, etc., with the material's mass thickness varying, and thus obtaining a series of collected values; calculating two function values from the signals for high and low energy levels collected each time, for example, calculating ln(HEL/HEL0) from the signals for high or low energy level, and calculating a*{ln(LEL/LEL0)−ln(HEL/HEL0)} from the signals for high energy level, where a is a coefficient and HEL0 and LEL0 each are predetermined reference detection values; then obtaining the fitting functions of the material based on the statistical values of the above two function values, as shown in FIG. 4.

Then, the classification curves are obtained from the fitting functions by use of statistical methods such as K-means or leader clustering, vector machine, etc. For example, computing the statistical variance of the fitting function value, and then displacing the fitting curve by the corresponding variance according to the optimum classification criterion as required. In discriminating an unknown material, the classification function values for the detection values are computed from the two function values of the detection values. Then the computed values are compared with the predetermined classification function values to obtain the effective atomic number range of the material and to further determine the material attributes of the object.

Figure 5:
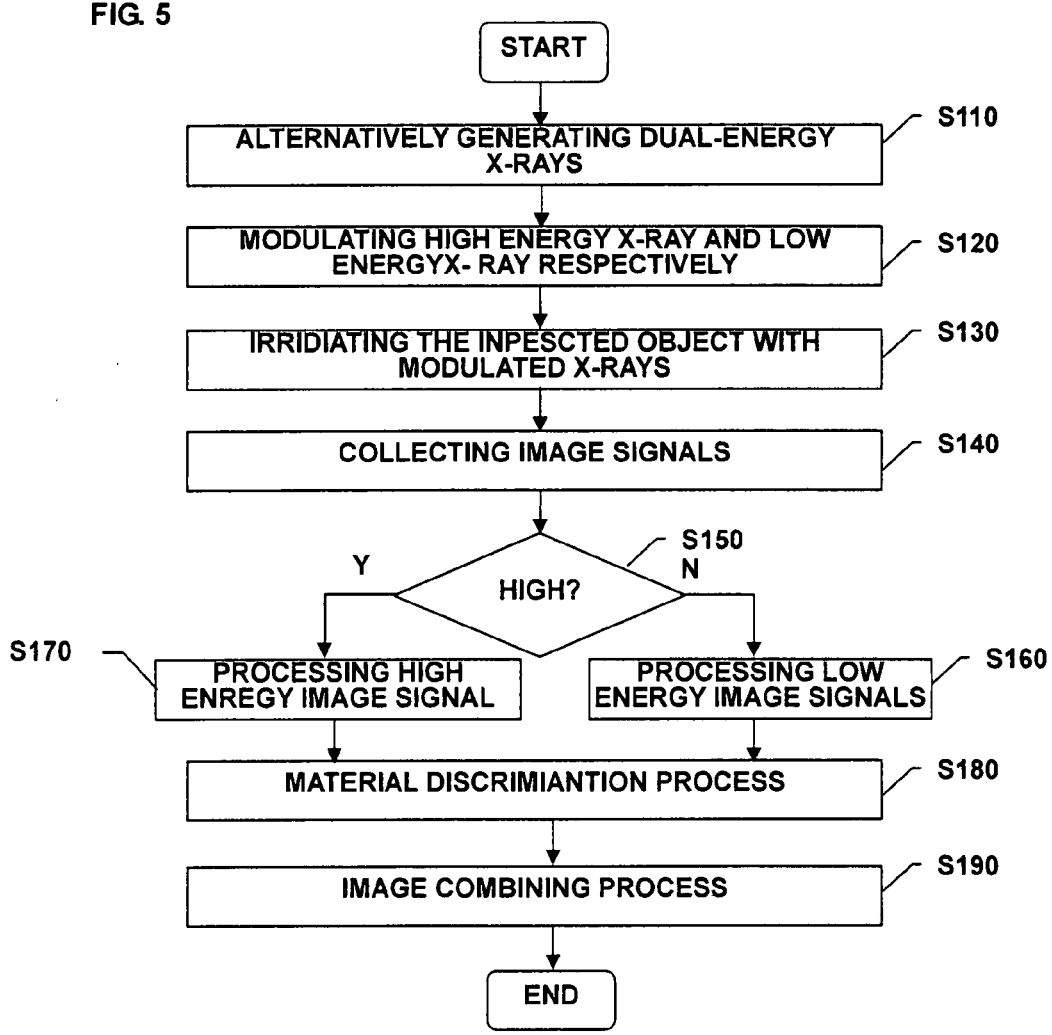
FIG. 5 is the flow chart of detecting and discriminating materials with two ray beams having different energy levels.

FIG. 5 is the flow chart of detecting and discriminating materials with two ray beams having different energy levels.

As shown in FIG. 5, in Step S110, the RF linac 1 can alternately generates X-rays having two different energy spectra, such as a first X-ray having a first energy spectrum and a second X-ray having a second spectrum, based on a trigger signal.

Then, in Step S120, the above-mentioned energy spectrum modulation apparatus 2 is utilized to modulate the X-rays having different energy spectra. For example, both controlled by the synchronization signal, the first energy spectrum modulation part 202 modulates the first X-ray while the second energy spectrum modulation part 203 modulates the second X-ray.

Next, in Step S130, after passing through the first and second collimators 6A and 6B, the modulated X-rays radiate and interact with the inspected object 7.

In Step S140, the detector 8 collects data for high and low energy levels based on the synchronization signal from the control system 9. Here, the detector 8 can change the multiple of its amplifying gain to change its dynamic range, thereby obtaining with higher accuracy the signal values after the interaction between the dual-energy rays and the object.

In Step S150, the imaging signals for high and low energy levels are sent to the material discrimination and image processing part 13, in which it is judged that whether the sent signal is imaging signal for high energy level or for low energy level.

The imaging signals for high and low energy levels are processed in Steps S160 and S170, respectively.

In Step S180, the classification function values for the detection values are computed from the two function values for high and low energy levels. Then the computed values are compared with the predetermined classification function values to obtain the effective atomic number range of the material and to further determine the material attributes of the object.

In Step S190, in order to obtain a clear image of the inspected object, a number of images obtained after the X-rays having different energy levels scan the inspected object can be combined to acquire a scan image of better quality.

It is well known that the penetration factor of high-energy rays is strong, and the detection data can be obtained with a high accuracy after the rays penetrate through an object of large mass thickness, therefore, a clear gray-scale image can be acquired for the object of large mass thickness. However, when high-energy rays penetrate through an object of small mass thickness, the obtained gray-scale image is blurred and the detail information tends to be lost. Fortunately, the above disadvantage can be compensated by the gray-scale image obtained after low-energy rays penetrate through the object.

Figure 6:
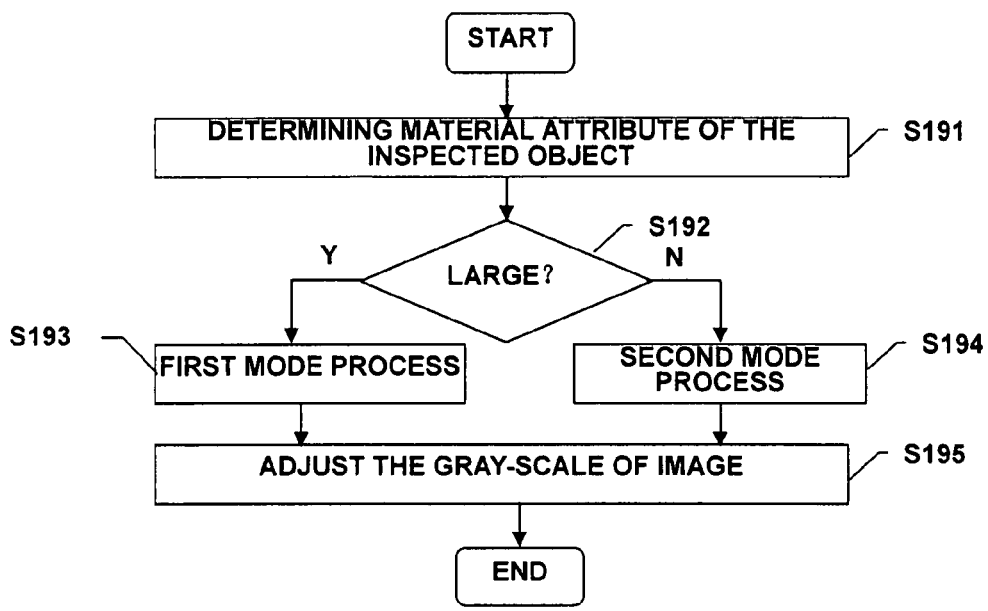
FIG. 6 is the flow chart of the method of adjusting images with different mass thickness information.

FIG. 6 is the flow chart of the method of adjusting images with different mass thickness information. In the image combination, the different attenuation characteristics of the high- and low-energy rays with respect to the different mass thickness of the object are used, and the clear image can be acquired in a wide range of mass thickness by fusing two kinds of detection values.

In Steps S191 and S192, the material attributes of the inspected object are determined, for example, whether the mass thickness of the inspected object 7 is thick or thin. Here, the approximate range of the mass thickness of the object is judged from the attenuation of the rays, that is, when the attenuation is great, for example, the detection value is less than a predetermined threshold value, the mass thickness of the material is referred as large; when the attenuation is little, for example, the detection value is more than a predetermined threshold value, the mass thickness of the material is referred as small.

In Step S193, for the material of a small mass thickness, a smaller weighting factor, such as 30%, is given to the data for the high energy level, and a bigger weighting factor, such as 70%, is given to the data for the low energy level.

In Step S194, for the material of a large mass thickness, a bigger weighting factor, such as 70%, is given to the data for the high energy level, and a smaller weighting factor, such as 30%, is given to the data for the low energy level.

Then, in Step S195, the images for the high and low energy levels are synthesized using the above weighting factors to acquire the final clear image.

Therefore, the present invention proposes that the detection values obtained after the X-rays of different energy levels interact with the object are compared with the corresponding predetermined threshold values, and different weighting factors are given to the data for the high and low energy levels, thereby obtaining the gray-scale information of the finally synthesized image.

Although the images, which are detected after the rays interact with objects of various mass thickness, have different image characteristics, with the processing of the above method, even if the mass thickness of objects varies greatly, a clear gray image of the material can be acquired in the object scanning.

The above-mentioned is only the specific embodiments of the present invention, while the scope of the present invention is not limited to it. Any modification or substitution, which is obvious to the skilled in the art within the technical range disclosed in the present invention, should be included in the scope of the present invention, which is thus defined by the claims.

What is claimed is:

1. An energy spectrum modulation method by using an energy spectrum modulation apparatus, wherein the energy spectrum modulation apparatus comprises a rotation shaft, a first energy spectrum part and a second energy spectrum part both coupled to the shaft, and the energy spectrum modulation method comprises the steps of:
    modulating by the first energy spectrum modulation part a first X-ray having a first energy spectrum; and
    modulating by the second energy spectrum modulation part a second X-ray having a second energy spectrum different from the first energy spectrum;
    wherein
    the first energy spectrum modulation part includes at least one first vane, and the second energy spectrum modulation part includes at least one second vane; and
    the mass thickness of the first vane is smaller than or equal to that of the second vane in the direction of the X-rays.

2. The energy spectrum modulation method of claim 1, wherein the first vane is made of material having a first Z value, the second vane is made of material having a second Z value lower than the first Z value.

3. The energy spectrum modulation method of claim 2, wherein the first vane is made of at least one of Pb, W, U and Cu.

4. The energy spectrum modulation method of claim 2, wherein the second vane is made of at least one of B, C, polyethylene and any other hydrogen-rich organic material.

5. The energy spectrum modulation method of claim 2, wherein the first vane and the second vane are arranged alternately and can rotate.

6. A method of discriminating material using X-rays having different energy levels comprising the steps of:
    generating alternately a first X-ray having a first energy spectrum and a second X-ray having a second energy spectrum;
    performing energy spectrum modulation for the first X-ray and second X-ray respectively by the energy spectrum modulation method of claim 1;
    utilizing the modulated first X-ray and second X-ray to interact with an inspected object;
    collecting the first X-ray and the second X-ray after their interaction with the inspected object to obtain a first detection value and a second detection value; and
    discriminating a material of the inspected object based on the first detection value and the second detection value;
    wherein the discriminating step includes generating corresponding classification functions from the first detection value and the second detection value, and determining the material of the inspected object based on the classification functions, the classification functions is fitting functions of third and fourth detection values obtained after the first X-ray and the second X-ray interact respectively with predetermined known materials having varying mass thickness.

7. The method of claim 6, wherein the detection values are the transmission intensity of the X-rays after they penetrate through the inspected object.

8. The method of claim 6, wherein the known materials are different materials which represent organic matter, light metal, inorganic matter and heavy metal respectively and whose atomic numbers are known.

9. The method of claim 6 further comprises collecting the first X-ray and the second X-ray after their interaction with the inspected object by a variable gain detector.

10. The method of claim 9, wherein the gain of the detector at the time of collecting the first X-ray is different from that at the time of collecting the second X-ray.

11. A device for discriminating material using X-rays having different energy levels comprising:
    a ray generation apparatus for generating alternately a first X-ray having a first energy spectrum and a second X-ray having a second energy spectrum;
    an energy spectrum modulation apparatus for modulating the first X-ray and the second X-ray respectively, wherein the modulated first X-ray and the modulated second X-ray interact with the inspected object;
    a collecting apparatus for collecting the first X-ray and the second X-ray after their interaction with the inspected object to obtain a first detection value and a second detection value; and
    a material discrimination apparatus for discriminating a material of the inspected object based on the first detection value and the second detection value;
    wherein the discriminating apparatus is further adapted to generate corresponding classification functions from the first detection value and the second detection value, and determine the material of the inspected object based on the classification functions, the classification functions are fitting functions of third and fourth detection values obtained after the first and second X-rays interact respectively with predetermined known materials having varying mass thickness.

12. The device of claim 11, wherein the detection values are the transmission intensity of the X-rays after they penetrate through the inspected object.

13. The device of claim 11, wherein the known materials are different materials which represent organic matter, light metal, inorganic matter and heavy metal respectively and whose atomic numbers are known.

14. The device of claim 11, wherein the collecting apparatus has a variable gain.

15. The device of claim 14, wherein the gain of the collecting apparatus at the time of collecting the first X-ray is different from that at the time of collecting the second X-ray.

16. An image processing method comprising the steps of:

utilizing a first X-ray having a first energy spectrum and a second X-ray having a second energy spectrum to interact with an inspected object, respectively, wherein the first X-ray and the second X-ray are modulated by the energy spectrum modulation method of claim 1;

collecting the first X-ray and the second X-ray after the interaction to obtain a first detection value and a second detection value;

comparing the first detection value and the second detection value with a threshold value respectively to judge mass thickness information of the inspected object; and based on the mass thickness information, combining an image obtained from the first detection value and an image obtained from the second detection value with different weighting factors; for a material having a first mass thickness, the weighting factor for the image from the first detection value is smaller than that for the image from the second detection value; for a material having a second mass thickness larger than the first mass thickness, the weighting factor for the image from the first detection value is greater than that for the image from the second detection value.

17. The image processing method of claim 16, wherein the mass thickness information is determined based on the attenuation of the X-rays from the inspected object.

* * * * *